United States Patent [19]

Gianni

[11] Patent Number: 4,466,538
[45] Date of Patent: Aug. 21, 1984

[54] HYPODERMIC NEEDLE DISPOSAL SYSTEM

[75] Inventor: Richard F. Gianni, Danville, Calif.

[73] Assignee: Biosafety Systems, Inc., San Diego, Calif.

[21] Appl. No.: 485,203

[22] Filed: Apr. 15, 1983

[51] Int. Cl.³ .................. B65D 25/00; B65F 1/02; B65F 7/00

[52] U.S. Cl. .................. 206/366; 206/370

[58] Field of Search .................. 206/370, 63.5, 366

[56] References Cited

U.S. PATENT DOCUMENTS 2,034,006  3/1936  Smith .................. 206/63.5
4,375,849  3/1983  Hanifl .................. 206/63.5

Primary Examiner—William T. Dixson, Jr.
Attorney, Agent, or Firm—Fulwider, Patton, Rieber, Lee & Utecht

[57] ABSTRACT

A hypodermic needle disposal system includes a portable disposable bottle having a cap assembly movable between an open position permitting used needles to be dropped into the bottle and a closed position locked against reopening. The cap assembly comprises a shim positioned over a bottle opening and a cap ring secured to the bottle in a position overlying the shim and rotatable between the open and closed positions, wherein the shim and cap ring have passages of predetermined shape formed off-center therein. In the open position, these off-center passages are aligned to permit dropping of used needles into the bottle which is shaped for controlled needle stacking for optimized numerical capacity. In the closed position, the off-center passages are moved out of alignment to close the bottle opening, and locking members on the cap ring and bottle are moved into locked engagement to prevent return cap ring movement toward the open position.

35 Claims, 15 Drawing Figures

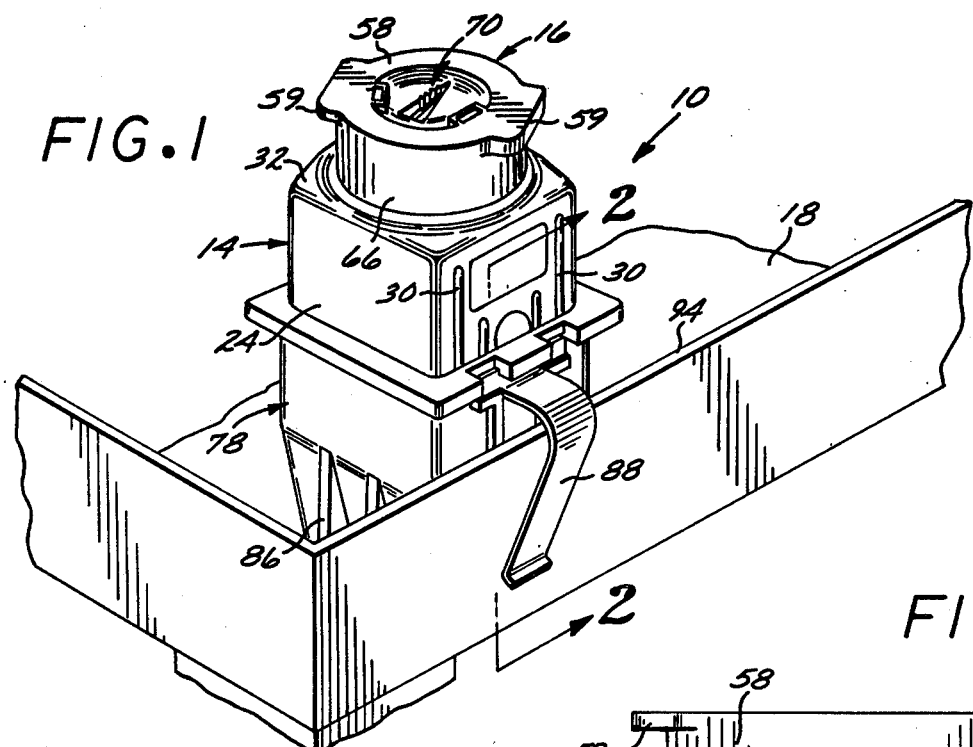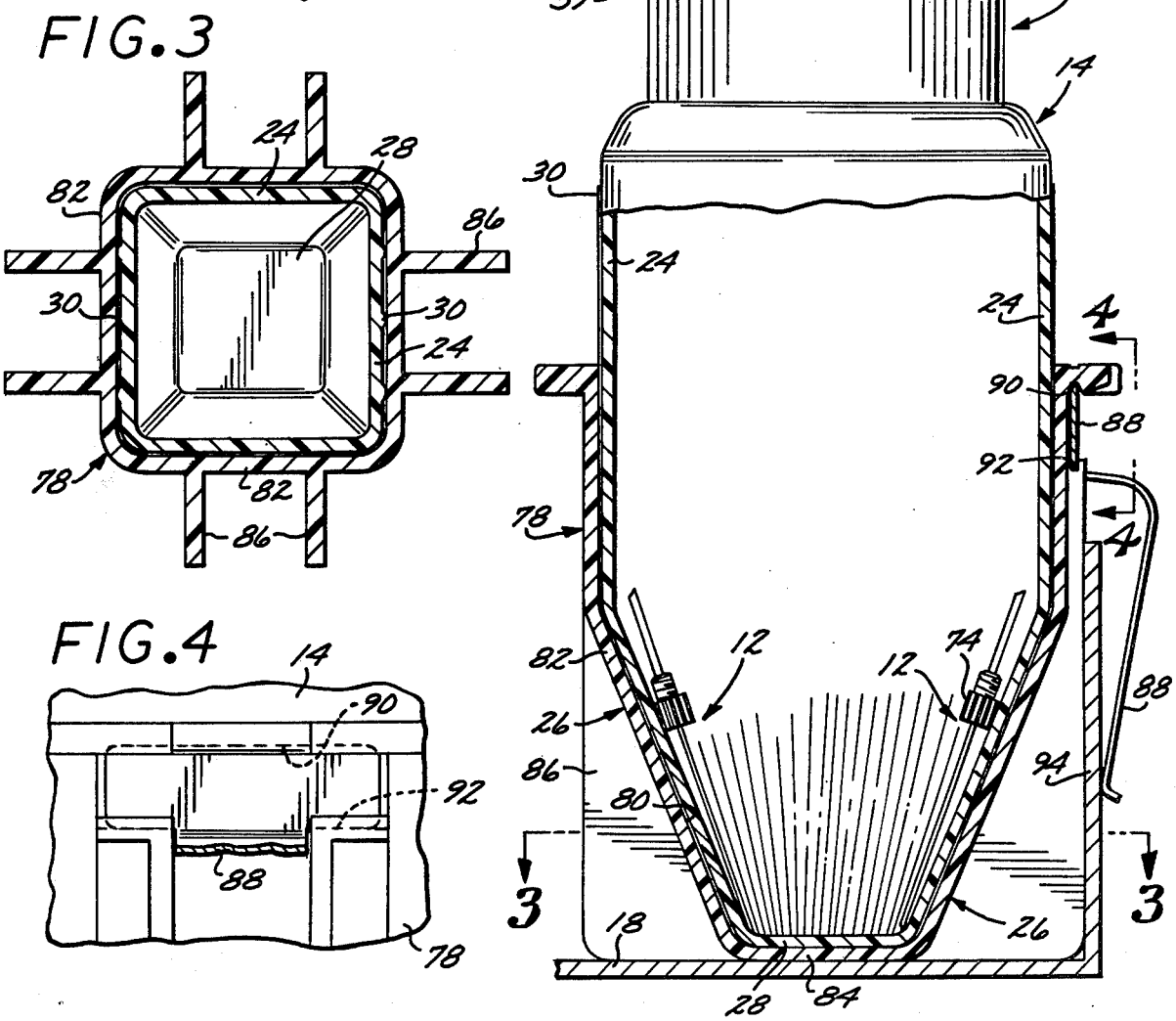

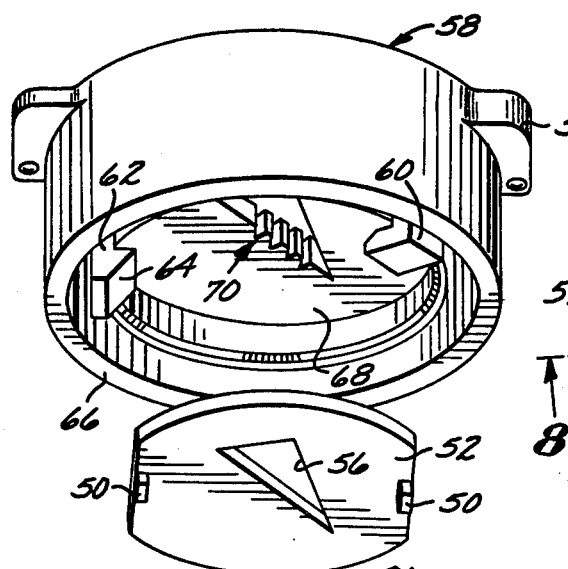
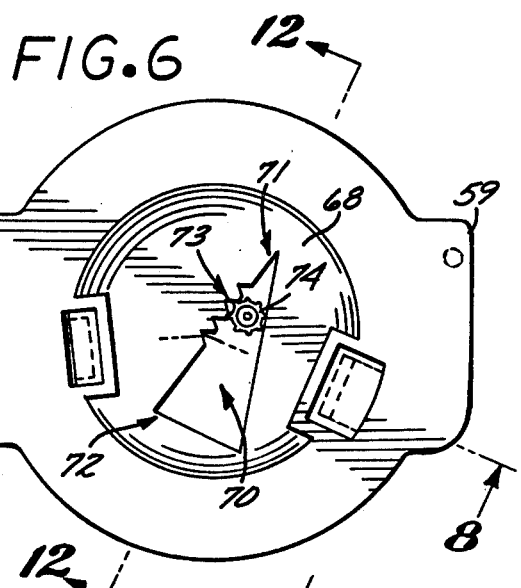
FIG.5   FIG.6
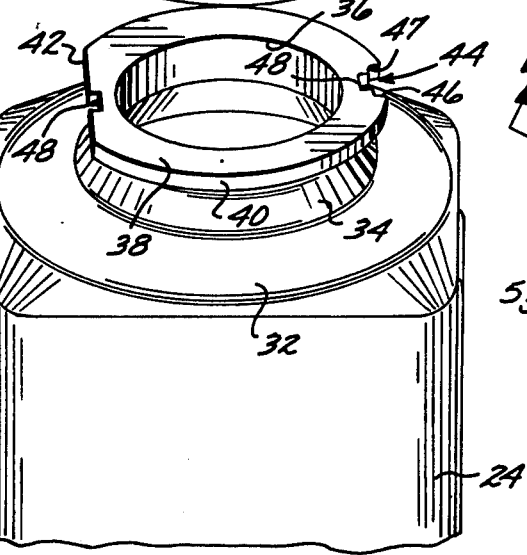
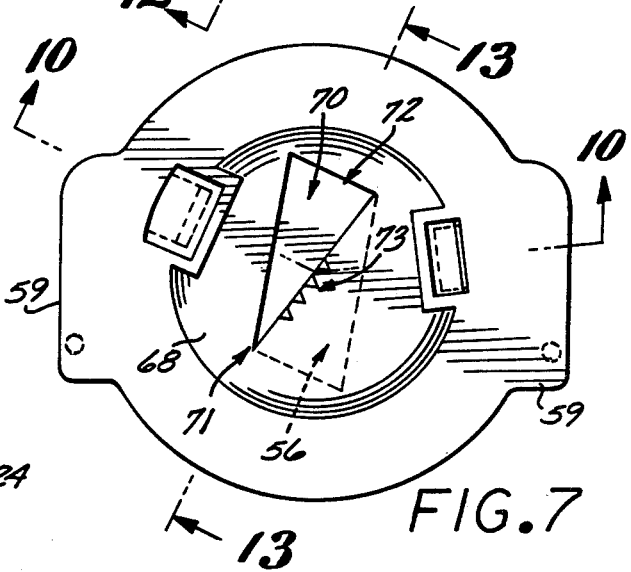
FIG.8   FIG.7
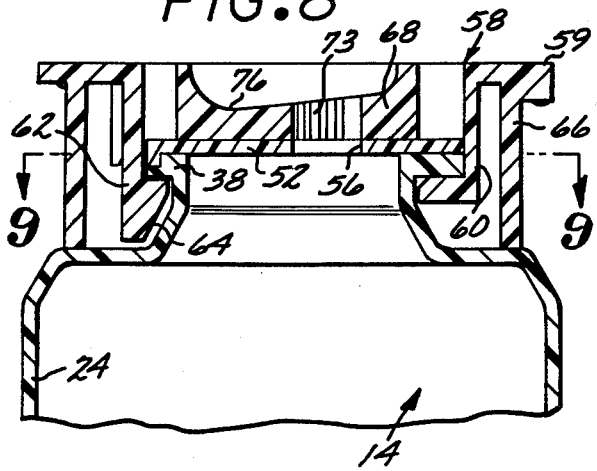
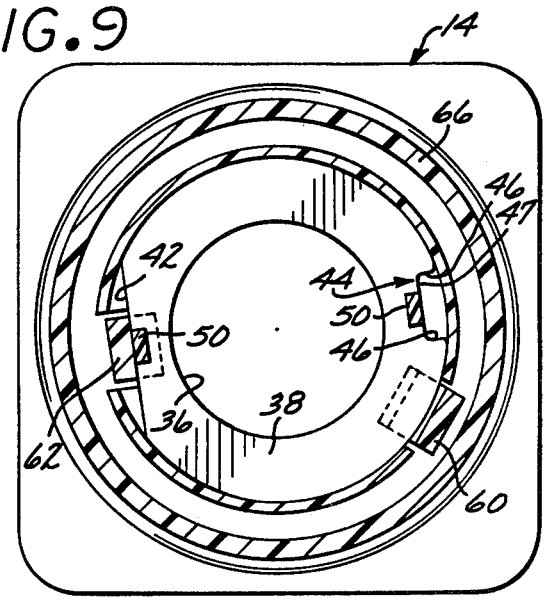
FIG.9

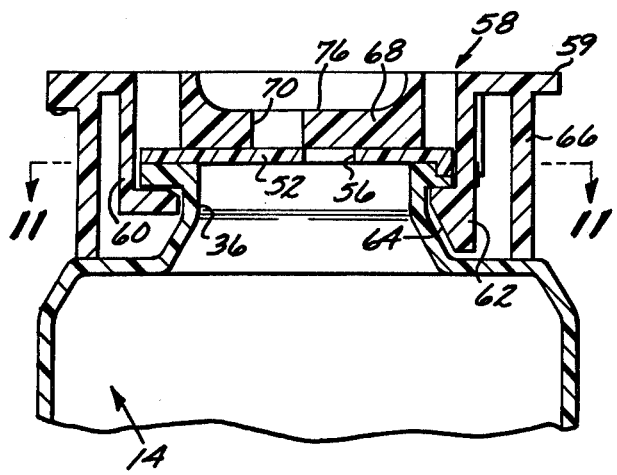
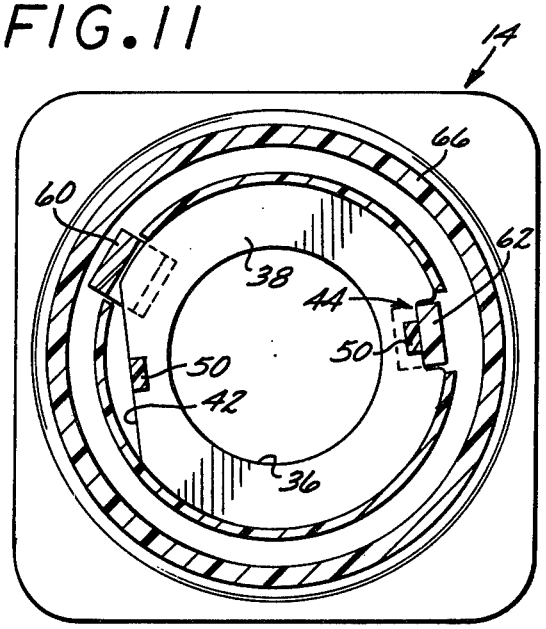
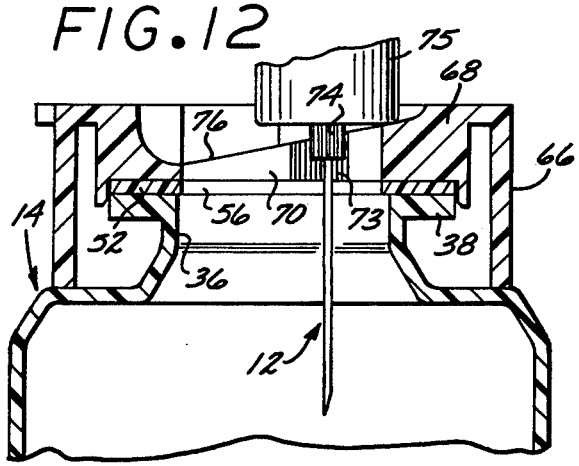
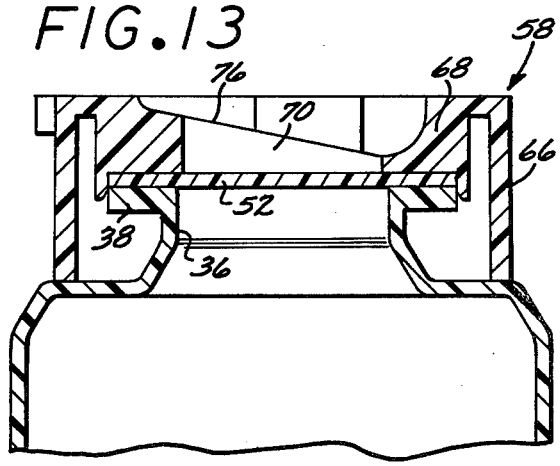
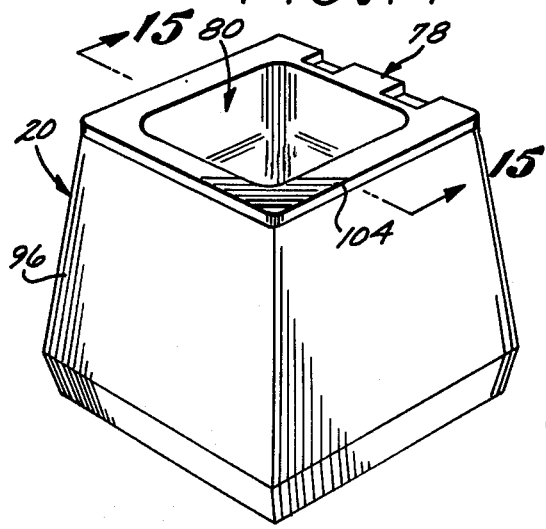
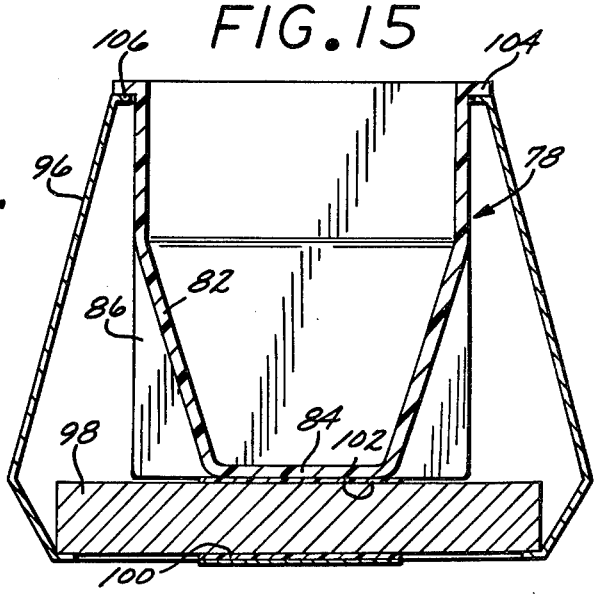

HYPODERMIC NEEDLE DISPOSAL SYSTEM

BACKGROUND OF THE INVENTION

This invention relates generally to systems and devices for use in the disposal of potentially hazardous items, and more particularly, this invention relates to a relatively simple and easy-to-use system for safe reception and subsequent disposal of used hypodermic needles and the like.

In medical examination and treatment facilities, such as a hospital, hypodermic needles are used widely on a regular basis for a variety of purposes including, for example, drawing of blood and other patient fluid samples, administration of medication, and the like. Such hypodermic needles are commonly provided as individually prepackaged, presterilized, disposable items intended for use a single time after which they are discarded, thereby avoiding relatively costly and time-consuming needle resterilization and the need for related sterilization equipment. However, disposal of the once-used hypodermic needles must be accomplished in a manner which safely avoids injury to medical personnel, such as inadvertent needle punctures and further which prevents potentially contaminating contact with the used needles. Moreover, it is highly desirable to dispose of the used needles in a manner which minimizes opportunity or risk of unauthorized reuse, for example, by users of illegal drug substances.

More particularly, by way of one specific example, medical technicians in a hospital facility are typically required to draw a relatively large number of patient blood samples each day. These blood samples are normally collected by the technician within individual sterilized containers on a portable tray or the like during his rounds from one patient room to another, wherein a separate disposable hypodermic needle is used to draw each blood sample. In accordance with a common blood drawing technique, the sterilized containers constitute individual vacuum tubes closed by a self-sealing cap and shaped for inverted insertion into an open-topped syringe barrel. Each hypodermic needle comprises a double-ended needle unit having a first needle for insertion into the patient, a second needle for reception into the syringe barrel piercing the cap of the vacuum tube, and an intermediate cartridge structure adapted for releasable connection as by threading to the lower end of the syringe barrel. Following drawing of each blood sample, the filled vacuum tube and the used needle unit are removed from the syringe barrel and replaced by a subsequent tube and needle unit preparatory to drawing a subsequent sample. The vacuum tubes when filled are stored temporarily on the technician's rounds to an appropriate laboratory facility, whereas the used needle units are also normally collected on the tray for later disposal in a controlled manner.

It is highly desirable to separate each used hypodermic needle unit from the syringe barrel in a manner requiring little or no human contact, thereby preventing inadvertent injury or contamination which otherwise occur. Moreover, after separation from the syringe barrel, it is highly desirable to substantially isolate the collected needle units from subsequent direct human contact, either intentional or inadvertent, and thereby further safeguard against undesired injury or contamination.

In the past, a variety of devices and systems have been proposed for use in disposing used hypodermic needles and the like. For example, disposable needle collection cups designed for carrying on a medical technician's tray or the like are well known. In some instances, these collection cups are designed to include a cap having a specially shaped opening for bearing engagement by the cartridge structure of a double-ended needle unit to permit unthreading of the needle unit from a syringe barrel as a one-handed operation, whereupon the thus-separated needle unit is intended to fall into the collection cup without direct handling by the technician. However, such cap constructions have not prevented occasional jamming of the needle unit within the cap opening such that it becomes necessary to dislodge the needle unit manually resulting in possible contamination or injury. Other collection cup designs have included a movable cap which can be closed when the cup is full to permit cup handling for disposal purposes without contacting the used needles. However, cap constructions of this type have been susceptible to relatively easy reopening, sometimes inadvertently, resulting in potential contamination, injury, or unauthorized reuse.

Alternative devices, such as needle clipping mechanisms, have been proposed for severing and destroying hypodermic needles promptly after use. While mechanisms of this type advantageously prevent unauthorized needle reuse, they have not safeguarded the severed needles from subsequent human contact, particularly during handling for disposal purposes. Moreover, needle clipping mechanisms in the past generally have been relatively cumbersome to operate and have had sufficient size and/or wieght such that they have not been conveniently transportable. As a result, needle clipping mechanisms have not been widely accepted for use by medical technicians and other medical personnel.

There exists, therefore, a significant need for an improved disposal system for collection and disposal of used hypodermic needles, wherein the used needles can be removed quickly and easily from a syringe barrel or the like substantially without direct human contact, and further wherein the collected needles can be substantially isolated from further access during handling for disposal purposes. The present invention fulfills this need and provides further related advantages.

SUMMARY OF THE INVENTION

In accordance with the invention, an improved disposal system is provided for rapid, convenient, and safe disposal of used hypodermic needles and the like. The disposal system comprises a portable disposable bottle having a bottle opening covered by a cap assembly through which used hypodermic needles can be dropped into the bottle. The cap assembly is secured onto the bottle for rotational movement between an open position permitting used needles to be dropped therethrough and a closed position substantially locked against reopening.

In accordance with a preferred form of the invention, the bottle is formed from a lightweight molded plastic or the like to include a generally rectangular cross-section shape defined by four side walls, the lower portions of which are angled downwardly and inwardly toward each other to provide a cross-sectional area progressively decreasing in a direction toward the bottle bottom. A cylindrical neck projects upwardly at the top of the bottle and defines a circular bottle opening of comparatively smaller cross-sectional area. The upper extent of the neck terminates in a radially outwardly flanged neck ring having a circular periphery interrupted by a generally flat chord and a relatively large notch formed at opposite sides of the bottle opening.

The cap assembly comprises a relatively thin platelike shim received over the neck ring and having a passage formed therein in an off-center position preferably with a generally triangular shape. The shim includes a pair of relatively small depending tabs which register with relatively small slots in the underlying neck ring to lock the shim against rotation relative to the neck ring.

The cap assembly further includes a cap ring sized to overlie the shim and including a pair of downwardly and radially inwardly projecting L-shaped locking legs having feet for locking engagement beneath the bottle neck ring. These locking legs are positioned at different radial distances from the center of the bottle opening with one of said legs having its foot normally engaged beneath the flat chord at one side of the neck ring. A depending peripheral skirt projects downwardly from the cap ring in surrounding relation with the locking legs to contact an upper flat surface of the bottle thereby concealing from view the locking legs, and their relative positions and functions.

A cover plate formed integrally with the cap ring overlies the shim and has a passage, preferably of generally triangular shape, formed therein to directly overlie the shim passage when said cap assembly is in the open position. This cap ring passage is contoured to include at least one serrated edge for binding engagement by a used hypodermic needle during separation thereof from a syringe barrel, in combination with an upper face angled downwardly toward a relatively wide passage base to insure downward needle movement through the passage into the disposable bottle. Such needles, dropped one at a time into the bottle fall against the bottle side walls which advantageously orient the needles for stacking in a controlled manner for substantially optimized numerical bottle capacity.

The cap ring is rotatable about the bottle neck ring from an open position with the cap ring and shim passages aligned to a closed position with the cap ring passage moved out of alignment with the shim passage. Such rotational movement is accompanied by movement of the locking leg normally engaged beneath the neck ring flat chord to a spring-loaded radially outward position guided about the curved neck ring periphery until said leg moves into alignment with and seats into the relatively large notch at the opposite side of the neck ring. The cap ring passage is thus rotated through approximately 180 degrees relative to the shim thereby moving the off-center cap ring passage into misalignment with the off-center shim passage and closing access to the bottle interior. The opposite marginal edges of the neck ring notch are bounded by radially directed shoulders which lock the leg against retraction from the notch upon further attempted cap ring rotation.

The bottle is adapted for convenient seated support within a portable base which is easily transported upon the equipment tray of a medical technician or the like and which further may include a spring clip for secured attachment to such tray. Alternatively, the bottle is adapted for seated reception into a stable support housing designed for nonskid movement on a desk, table, or the like, wherein the support housing conveniently may be designed for removable reception of the portable base which in turn supports the bottle.

Other features and advantages of the hypodermic needle disposal system of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is fragmented perspective view illustrating a hypodermic needle disposal system including a disposable bottle and cap assembly embodying the novel features of the invention and shown supported by a portable base adapted for locking onto a portable medical tray or the like;

FIG. 2 is an enlarged vertical section, partially in side elevation, taken generally on the line 2—2 of FIG. 1 and illustrating the bottle supported within the portable base;

FIG. 3 is a horizontal section taken generally on the line 3—3 of FIG. 2;

FIG. 4 is an enlarged fragmented elevation view of a portion of the system taken generally on the line 4—4 of FIG. 2 and illustrating a spring clip on the portable base for locking engagement with a medical tray or the like;

FIG. 5 is an enlarged fragmented exploded perspective view illustrating assembly of the disposable bottle and cap assembly;

FIG. 6 is a top plan view illustrating the cap assembly in an open position;

FIG. 7 is a top plan view illustrating the cap assembly in a closed position;

FIG. 8 is a fragmented vertical section taken generally on the line 8—8 of FIG. 6;

FIG. 9 is a horizontal section taken generally on the line 9—9 of FIG. 8;

FIG. 10 is a fragmented vertical section taken generally on the line 10—10 of FIG. 7;

FIG. 11 is a horizontal section taken generally on the line 11—11 of FIG. 10;

FIG. 12 is a fragmented vertical section taken generally on the line 12—12 of FIG. 6;

FIG. 13 is a fragmented vertical section taken generally on the line 13—13 of FIG. 7;

FIG. 14 is a perspective view illustrating a support housing for use with the bottle and cap assembly; and FIG. 15 is an enlarged vertical section taken generally on the line 15—15 of FIG. 14.

DETAILED DESCRIPTION OF THE PREFERRED EMBODIMENT

As shown in the exemplary drawings, a disposable system referred to generally by the reference numeral 10 is provided for convenient and safe disposal of used hypodermic needles 12 and the like. The system includes a disposable bottle 14 together with a specially designed cap assembly 16 which is movable from an open position permitting used needles 12 to be dropped into the bottle 14 to a closed position substantially locked against subsequent reopening. The bottle 14 is adapted for ready transport on and connection relative to a portable medical equipment tray 18 or the like, as shown in FIG. 1, or alternatively, the bottle 14 may be supported on a laboratory desk or the like within a stable nonskid support housing 20, as viewed in FIGS. 14 and 15.

The disposal system 10 of the present invention provides a relatively inexpensive yet highly convenient, easy-to-use, and safe apparatus for disposal of used hypodermic needles and the like in a medical examination and treatment facility, such as a hospital. The system is advantageously designed for facilitated dropping of used hypodermic needles into the disposable bottle 14 quickly and easily without requiring manual handling of the needles at any time. When the bottle 14 is filled with used needles, the cap assembly 16 is designed for closure quickly and easily to lock the bottle permanently against reopening and thereby safeguard the used needles therein from human contact during subsequent handling of the bottle for disposal which can be achieved by incineration or other suitable means. Potential injuries to medical personnel, such as needle punctures and potential contamination of such personnel and/or medical equipment which might otherwise occur from direct contact with the needles, is thereby avoided. Moreover, once the cap assembly is closed and locked, access to the used needles in the bottle is denied to correspondingly prevent inadvertent needle reuse and further to prevent unauthorized intentional reuse, for example, by users of illegal drug substances.

The disposal system 10 is particularly adapted for use by medical technicians or similar medical personnel required to use a relatively large number of syringes or hypodermic needles of the type intended for disposal after a single use. More particularly, by way of one specific example, medical technicians in hospitals are typically required to draw relatively large numbers of patient blood samples in a relatively short period of time during rounds from one patient room to another. In accordance with one well-known procedure, the technician carries a portable tray or the like provisioned with a supply of sterilized vacuum tubes, each closed by an elastomeric sealing cap, and a supply of single-use double-ended hypodermic needle units. Each blood sample is drawn by connecting one of the needle units, as by threading, to the bottom of an open-topped syringe barrel such that one needle projects into the barrel and another needle projects outwardly for insertion into a patient. A vacuum tube is inserted in an inverted fashion into the syringe barrel for piercing of the elastomeric cap by the adjacent needle whereupon the tube vacuum draws the desired blood sample. The vacuum tubes when filled are stored on the technician's tray for the duration of the rounds and for subsequent transport to an appropriate laboratory facility, whereas the used needle units are desirably collected on the tray for subsequent controlled disposal. The disposal system 10 of this invention is conveniently carried on the tray for safe collection and subsequent disposal of these used hypodermic needle units.

In the presently preferred form of the invention, as shown by the accompanying exemplary drawings, the bottle 14 is formed from a relatively lightweight plastic material, such as polyethylene formed by a convenient blow molding process or the like, to include a bottle body having a generally rectangular crosssection defined by four sides 24. As shown best in FIGS. 2 and 3, these four sides 24 are oriented generally in parallel with one another over at least the upper half of the bottle body and include lower portions tapering downwardly and inwardly toward each other, as illustrated by arrows 26 in FIG. 2, to provide a cross-sectional area which progressively decreases toward a relatively small bottom wall 28. Vertically extending ribs 30 are conveniently provided on at least two opposite sides 24 of the bottle for added structural rigidity. If desired, the plastic material from which the bottle is formed may be opaque to conceal the bottle contents from view.

At the upper end of the bottle 14, the bottle sides 24 blend integrally with a generally horizontal annular upper wall 32 which surrounds an upwardly projecting, generally cylindrical central neck 34. This neck 34 defines a circular bottle opening 36 of relatively cross-sectional area in comparison with the rectangular bottle cross section near the top of the bottle 14. In addition, the upper extent of the cylindrical neck 34 terminates in a radially outwardly projecting neck flange or ring 38 spaced vertically above the annular upper wall 32 of the bottle and specially configured for locking with the cap assembly 16.

More particularly, as shown best in FIG. 5, the neck ring 38 has a substantially circular periphery 40 interrupted at one side of the bottle opening 36 by a generally flat chord 42 occupying on the order of about 65 degrees of the neck ring periphery. A relatively large notch 34 also interrupts the neck ring periphery and is disposed at an opposite side of the bottle opening approximately 180 degrees from a center of the flat chord 42. The opposite margins 46 of this notch 44 are defined by relatively small shoulders projecting radially outwardly relative to a center of the bottle opening 36, and the base 47 of the notch is formed at a radial distance not less than and preferably slightly greater than the radial distance of the center of the flat chord 42 from a center of the bottle opening 36.

Both the flat chord 42 and the notch 44 of the neck ring 38 are in turn interrupted centrally by a respective pair of comparatively small slots 48. These slots 48 are provided for registry with and reception of a corresponding pair of depending tabs 50 formed on a relatively thin shim 52 comprising a portion of the cap assembly 16. This shim 52, which may be formed conveniently from a suitable molded plastic or the like is placed over the bottle opening 36 and the neck ring 38 with its tabs 50 received into the slots 48 to prevent relative rotation between the shim 52 and the bottle 14. Importantly, the shim 52 includes a passage 56 having preferably a generally triangular shape and disposed in an off-center position such that the passage 56 lies substantially in its entirety at one side of the center of the bottle opening 36.

The cap assembly 16 further comprises a cap ring 58 of a suitable molded plastic or the like for locking onto the neck ring 38 in a position overlying the shim 52. More particularly, the cap ring 58 includes a pair of downwardly projecting, generally L-shaped locking legs 60 and 62 each having a vertically extending riser joined at its lower end to a radially inwardly turned foot, wherein the foot of the leg 62 has a lower face 64 ramped downwardly in a radially outward direction. The locking leg 60 is formed with its vertical riser disposed on a radius for slight clearance with the curved periphery 40 of the neck ring 38, whereas the locking leg 62 is formed with its riser at a different radial position for slight clearance relative to the center of the flat chord 42 of the neck ring 38. Moreover, as shown best in FIGS. 6 and 7, the two locking legs 60 and 62 are angularly separated from each other by a spacing less than 180 degrees.

The cap ring 58 is locked onto the neck ring 38, in overlying relation to the shim 52, by angularly canting the cap ring above the neck ring to place the locking leg 60 with its foot in locked engagement beneath the curved periphery 40 at a position with the other locking leg 62 oriented generally centrally above the neck ring flat chord 42. The cap ring 58 can then be pushed downwardly in the region of the neck ring chord 42 whereupon the ramped lower face 64 of the leg 62 is springably retracted in a radially outward direction to allow the lower foot of the leg 62 to move over the flat chord and then snap back to a locked position centrally beneath the flat chord 42. In this manner, the cap 58 is locked quickly and easily onto the neck ring 38 with both locking legs 60 and 62 in a normally unstressed condition. A peripheral skirt 66 on the cap ring 58 projects downwardly in radially surrounding relation with the locking legs 60 and 62 into surface contact with the upper wall 32 of the bottle 14 to conceal the construction and position of the locking legs, thereby enhancing the difficulty in removing the cap ring from the bottle.

The locking legs 60 and 62 and the skirt 66 of the cap ring 58 are formed integrally with an upper central cover plate 68 which overlies the shim 52. This cover plate 68 has an off-center passage 70 formed therein with a size and shape generally corresponding with the off-center passage 56 in the underlying shim 52. Importantly, when the cap ring 58 is in the open position defined by installation onto the neck ring with the locking leg 62 centrally engaging the neck ring chord 42, as described above, the off-center passage 70 in the cover plate 68 directly overlies and is vertically aligned with the off-center passage 56 in the shim 52 to permit access to the bottle interior.

In the illustrative perferred form of the invention, the off-center passage 70 in the cover plate 68 is relatively narrow near an apex thereof, as referred to by arrow 71 in FIG. 6, and is comparatively wider at a passage base generally opposite the apex, as referred to by arrow 72. Moreover, one side margin of the side passage 70 near the apex 71 is contoured to define a serrated edge 73. This passage geometry facilitates secure gripping engagement between the cap ring 58 and the threaded cartridge 74 of a used double-ended needle unit of the type used commonly in drawing blood samples in patients, wherein the cartridge 74 is provided for threaded connection to a syringe barrel 75 or the like. More particularly, as shown best in FIGS. 6 and 12, the syringe barrel can be held to orient the needle unit cartridge 74 within the narrower apex region of the cover plate passage 70, whereupon the syringe barrel can be rotated (not shown) as a convenient one-handed operation to separate the used needle unit therefrom. When the needle unit separates from the syringe barrel, the needle unit falls by gravity through the passages 70 and 56 in the cover plate 68 and shim 52 downwardly into the bottle 14 without requiring any direct human contact with the used needle unit. The desired falling of the needle unit is advantageously assured by an angular oriented upper face 76 (FIG. 8) on the cover plate and ramped downwardly toward the wider base region of the passage 70 whereby the needle unit and syringe barrel tend to move away from the passage apex region during the unthreading procedure.

The used needles 12 dropped into the bottle 14 are caused to stack relative to each other in a controlled manner for optimizing the number of needles which can be collected in a compact bottle volume. That is, with reference to FIG. 2, the needles are necessarily dropped into the bottle in a generally vertical attitude as a result of the relatively narrow open area provided by the cap ring and shim passages 70 and 56. The falling needles first enter the upper, relatively large cross section region of the bottle and then fall further downwardly into the lower region of the bottle whereat the cross-sectional area progressively decreases. The generally vertically oriented needles 12 tend to strike and rest against one of the angled lower portions of the side walls 24 in a still generally vertical orientation without falling to a horizontal position bridged between the side walls. Subsequently dropped needles 12 tend to fall against the vertically oriented previously dropped needles to maintain a generally vertical stacking arrangement. The angular orientation of initially dropped needles in accordance with the lower portions of the side walls 24 conveniently causes upper layers of dropped needles to fall angularly against the upper portions of the side walls 24 with a similar angular orientation such that a central volumetric region within the bottle immediately below the bottle opening 36 is not occupied with used needles until the remaining volume of the bottle is filled substantially to capacity.

When the bottle 14 is filled with used hypodermic needles 12, or alternately when it is otherwise desired to disposed of the used needles 12 contained within the bottle, the cap ring 58 is rotated approximately 180 degrees relative to the bottle neck ring 38 to the closed position, as illustrated in FIGS. 7, 10, 11 and 13. This rotation, which is desirably facilitated by wings 59 formed on the cap ring 58 for easy manual grasping, initially moves the locking leg 62 along the flat chord 42 to a radially outward position spring-loaded against the curved periphery 40 of the neck ring. Further rotation of the cap ring 58 moves the now spring-loaded leg 62 about the ring periphery to alignment with the notch 44 at the opposite side of the neck ring wherein the spring force causes the riser portion of the leg 62 to snap into the notch in a position with the lower foot thereof engaged beneath the neck ring 38. Once seated within the notch 44, the radial shoulders 46 at the side margins of the notch prevent subsequent rotational movement of the cap ring thereby positively and permanently locking the cap ring in the closed position.

The above-described rotational movement of the cap ring 58 rotates the off-center cap ring passage 70 approximately 180 degrees relative to the off-center passage 56 in the underlying shim 52. Accordingly, as shown best in FIG. 6 and 7, the passage 70 in the cap ring 58 is moved out of vertical alignment with the shim passage 56 to close the bottle opening 36 and deny access to the bottle interior. The bottle 14 is thereby closed and locked against reopening to isolate the used needles 12 contained therein against human contact during subsequent handling of the bottle for disposal and/or destruction of the used needles. Inadvertent reopening of the bottle 14 is prevented by the seated and locked engagement between the locking leg 62 and the neck ring notch 44, whereas intentional bottle reopening is also substantially prevented particularly by individuals lacking knowledge of the bottle design by the cap ring skirt 66 which shields and conceals the cap ring locking structure.

The disposable bottle 14 is conveniently designed for seated support within a relatively lightweight portable base 78 adapted for portable transport on and connection to a medical equipment tray 18 or the like for inexpensive disposal, as shown in FIGS. 1–4. This portable base 78, which can be formed from a lightweight molded plastic or the like, is shaped to include an upwardly open cavity 80 for mating reception of the contoured lower end portion of the bottle 14. In this regard, the illustrative base 78 includes four side walls 82 defining a generally rectangular cross-sectional cavity, the lower portion of which progressively decreases in cross section toward a relatively small bottom wall 84. Outer support ribs 86 on the base side walls 82 provide the base 78 with a sufficiently broad base support structure for preventing tipping of the base 78 or the supported bottle 14 during use. A spring clip 88 is conveniently provided for snapfit reception into opposed grooves 90 and 92 molded into one side wall 82 of the base 78 for appropriate releasable connection to an upstanding flange 94 or other upstanding structure on a portable medical equipment tray 18 or the like.

Alternatively, the disposable bottle 14 may be supported within a stable support housing 20, as shown in FIGS. 14 and 15, wherein the support housing 20 is designed to rest without skidding on a table, desk, or the like in, for example, a medical laboratory. The preferred support housing 20 comprises an upwardly open housing 96 of any suitable and decorative material within which is mounted a lower weight 98 to provide the support housing 20 with the desired degree of stability. Highly effective nonskid characteristics may be obtained by use of a strip of double-stick tape 100 or the like on the bottom side of the weight 98.

The housing 96 is upwardly open, in the preferred form, for reception of the lightweight plastic base 78 described with respect to FIGS. 1-4. This base 78, absent the spring clip 88, is sized and shaped to fit into the housing 96 with its bottom wall 84 resting upon the weight 98 and a strip of double-stick tape 102 conveniently provided therebetween to secure the base 78 in place. An upper flange 104 on the base 78 rests upon a relatively small peripheral shelf 106 at the upper end of the support housing 30.

The hypodermic needle disposal system 10 of this invention thus provides relatively inexpensive disposable apparatus in the form of the bottle 14 and cap assembly 16 for safe and convenient reception of used hypodermic needles and the like without human handling. When bottle disposal is desired, the cap assembly 16 is quickly and easily closed in a position locked against reopening to substantially isolate the collected needles within the bottle from human contact or access during handling of the bottle for disposal purposes.

A variety of modifications and improvements to the invention described herein are believed to be apparent to one of ordinary skill in the art. For example, the bottle 14 and cap assembly 16 are adapted for use with needle clipping mechanisms and the like such as that described in copending and commonly assigned application Ser. No. (Docket No. 24461), entitled: HYPODERMIC NEEDLE CUTTING ASSEMBLY, which is incorporated by reference herein, wherein the disposal system of this invention provides a safe and convenient apparatus for collection and subsequent disposal of used hypodermic needles and the like. Accordingly, no limitation on the invention is intended, except by way of the appended claims.

What is claimed is:

1. A disposal system for used hypodermic needles and the like, comprising:
   a bottle having an upwardly open bottle opening formed therein;
   a cap assembly mounted on said bottle and including a first member secured against rotation relative to said bottle in a position overlying the bottle opening and having a relatively small first passage formed therein off-center relative to the bottle opening, and a second member overlying said first member and having a relatively small second passage formed therein off-center relative to the bottle opening, said second member being rotatable relative to said bottle and first member for movement from an open position with the first and second passages aligned to permit dropping of needles into the bottle to a closed position, with the second passage moved out of alignment with the first passage to prevent dropping of needles into the bottle; and
   means cooperating between said second member and said bottle for substantially locking said second member in said closed position against further rotation.

2. The disposal system of claim 1 wherein said first member comprises a relatively thin shim.

3. The disposal system of claim 2 wherein said second member comprises a cap ring rotatably mounted on said bottle, said shim being interposed between said cap ring and bottle.

4. The disposal system of claim 3 wherein said shim includes at least one tab for reception into a mating slot formed in said bottle to lock said shim against rotation relative to said bottle.

5. The disposal system of claim 1 wherein said locking means is substantially inaccessible from the exterior of said bottle and cap ring.

6. The disposal system of claim 1 wherein said locking means is responsive to movement of said second member to the closed position for substantially locking said second member in the closed position.

7. The disposal system of claim 1 wherein the first and second passages have a generally common size and shape formed respectively in said first and second members in positions disposed substantially entirely at one side of the bottle opening.

8. The disposal system of claim 7 wherein the first and second passages have a generally triangular shape including a relatively narrow apex region and a comparatively wider base region.

9. The disposal system of claim 8 wherein said second passage is defined in part by at least one serrated edge generally adjacent the apex region.

10. The disposal system of claim 8 wherein said second member includes an inclined upper face extending angularly downwardly from the apex region toward the base region of the second passage.

11. The disposal system of claim 1 wherein said bottle includes an upwardly projecting neck surrounding the bottle opening and including a radially outwardly flanged neck ring, said locking means cooperating between said second member and said neck ring.

12. The disposal system of claim 11 wherein said neck ring has a radially outwardly open notch formed in the periphery thereof, said notch being defined in part by a pair of circumferentially spaced, radially extending shoulders, and wherein said locking means comprises a locking leg extending downwardly from said second member for force-biased engagement with the periphery of said neck ring during movement of said second member from the open to the closed position, said locking leg being seatable within the notch when said second member is in the closed position.

13. The disposal system of claim 12 wherein said second member further includes a depending peripheral skirt surrounding said locking leg and projecting downwardly toward said bottle to conceal said locking leg from view.

14. The disposal system of claim 11 wherein said neck ring has a radially outwardly open notch formed in the periphery thereof, said notch being defined in part by a pair of circumferentially spaced, radially extending shoulders, and wherein said second member has a pair of locking legs extending downwardly therefrom each including a foot for engagement beneath said neck ring, one of said locking legs extending downwardly from said second member for force-biased engagement with the periphery of said neck ring during movement of said second member from the open to the closed position, said one locking leg being seatable within the notch when said second member is in the closed position.

15. The disposal system of claim 14 wherein said neck ring has its periphery interrupted by a generally flat chord at a side of the bottle opening generally opposite the notch, said one locking leg being positioned in an unstressed condition generally centrally relative to said chord when said second member is in the open position, said notch being further defined by a base extending between said shoulders at a radial distance relative to the center of the bottle opening generally at least as great as the radial distance of the center of said chord from the center of the bottle opening.

16. The disposal system of claim 14 wherein the foot of one of said locking legs has a ramped lower surface extending generally in a radially outward and downward direction.

17. The disposal system of claim 1 wherein said bottle has a generally rectangular cross-sectional shape defined by four side walls having generally parallel upper portions and lower portions angled generally inwardly and downwardly toward each other and joined to a relatively small bottom wall.

18. The disposal system of claim 17 further including a base member shaped to define an upwardly open cavity for mating reception of the lower end of said bottle, said base member including means for supporting said base member in a stable manner.

19. The disposal system of claim 18 wherein said base member includes attachment means for removable attachment of said base member to selected support structure.

20. A disposal system for used hypodermic needles and the like, comprising:
a bottle having a bottle opening formed therein; and
a cap assembly including means for mounting onto said bottle generally over the bottle opening and substantially locked against removal from said bottle, said cap assembly being movable from an open position to a closed position respectively permitting and preventing placement of needles into said bottle, said cap assembly including locking means for substantially locking said cap assembly in the closed position against movement to the open position in response to cap assembly movement from the open position to the closed position.

21. The disposal system of claim 20 wherein said locking means is substantially inaccessible from the exterior of said bottle and cap assembly.

22. The disposal system of claim 20 wherein said cap assembly comprises a relatively thin shim supported on said bottle against rotation relative thereto and having a relatively small shim passage formed therein in a position generally to one side of the center of the bottle opening, and a cap ring mounted on said bottle for rotation relative thereto and including a cap ring passage formed therein in a position generally to one side of the bottle opening center, said cap ring being movable from the open position with the cap ring and shim passages aligned to the closed position with the cap ring passages moved out of alignment with the shim passage.

23. The disposal system of claim 22 wherein said cap ring and shim passages have a generally common triangular shape including a relatively narrow apex region and a comparatively wider base region, said cap ring including a face surface opposite said shim angled generally downwardly from the apex region to the base region of the cap ring passage.

24. The disposal system of claim 23 wherein said cap ring passage is defined in part by at least one serrated edge generally adjacent the apex region.

25. The disposal system of claim 22 wherein said bottle includes an upwardly projecting neck surrounding rounding the bottle opening and including a radially outwardly flanged neck ring, said neck ring having a radially outwardly open notch formed in the periphery thereof, said notch being defined in part by a pair of circumferentially spaced, radially extending shoulders, and wherein said cap ring has a pair of locking legs extending downwardly therefrom each including a foot for engagement beneath said neck ring, one of said locking legs extending downwardly from said cap ring for force-biased engagement with the periphery of said neck ring during movement of said cap ring to the closed position, said one locking leg being seatable within the notch when said second member is in the closed position.

26. The disposal system of claim 25 wherein said neck ring has its periphery interrupted by a generally flat chord at a side of the bottle opening generally opposite the notch, said one locking leg being positioned in an unstressed condition generally centrally relative to said chord when said cap ring is in the open position, said notch being further defined by a base extending between said shoulders at a radial distance relative to the center of the bottle opening generally at least as great as the radial distance of the center of said chord from the center of the bottle opening.

27. The disposal system of claim 20 wherein said bottle has a generally rectangular cross-sectional shape defined by four side walls having generally parallel upper portions and lower portions angled generally inwardly and downwardly toward each other and joined to a relatively small bottom wall.

28. The disposal system of claim 27 further including a base member shaped to define an upwardly open cavity for mating reception of the lower end of said bottle, said base member including means for supporting said base member in a stable manner.

29. The disposal system of claim 20 wherein said bottle is opaque.

30. A disposal system for used hypodermic needles and the like, comprising:
a bottle having a generally rectangular cross section defined by four sides extending between a bottom wall and an upper wall and a generally cylindrical neck extending upwardly from said upper wall surrounding a bottle opening and including an outwardly radiating neck ring, said neck ring having a generally circular periphery interrupted respectively generally on opposite sides of the bottle opening by a radially outwardly open notch and a generally flat chord;

a relatively thin shim overlying said neck ring and including means cooperable with said neck ring to prevent rotation of said shim relative to said bottle, said shim having a passage formed therein generally off-center relative to the center of the bottle opening;

a cap ring including a cover plate overlying said shim, a pair of locking feet extending downwardly from said cover plate each including an inwardly radiating foot for engagement beneath said neck ring, said locking feet being disposed less than 180 degrees from each other relative to the center of the bottle opening and said cover plate having a passage formed therein generally off-center relative to the center of the bottle opening;

said cap ring being rotatable relative to said neck ring from an open position with the cap ring passage aligned with the shim passage to permit needles to be dropped into the bottles and a closed position with the cap ring passage moved out of alignment with the shim passage to prevent needles from being dropped into the bottle, one of said locking legs being forcebiased during movement of said cap ring from the open position to the closed position for seated reception into the neck ring notch when said cap ring reaches the closed position; and a peripheral skirt surrounding said locking legs for concealing said locking legs from view.

31. The disposal system of claim 30 wherein said cap ring and shim passages have a generally common triangular shape including a relatively narrow apex region and a comparatively wider base region, said cap ring including a face surface opposite said shim angled generally downwardly from the apex region to the base region of the cap ring passage.

32. The disposal system of claim 31 wherein said second passage is defined in part by at least one serrated edge generally adjacent the apex region.

33. The disposal system of claim 30 wherein said one locking leg is positioned in an unstressed condition generally centrally relative to said chord and the other locking leg is positioned in spaced relation with said notch when said cap ring is in the open position.

34. The disposal system of claim 30 wherein said bottle side walls include lower portions angled downwardly and inwardly toward each other to provide a region of progressively decreasing cross-sectional area in a direction toward said bottom wall.

35. The disposal system of claim 34 further including a base member shaped to define an upwardly open cavity for mating reception of the lower end of said bottle, said base member including means for supporting said base member in a stable manner.

* * * * *

UNITED STATES PATENT AND TRADEMARK OFFICE
CERTIFICATE OF CORRECTION

PATENT NO. : 4,466,538
DATED : August 21, 1984
INVENTOR(S) : Richard F. Gianni

It is certified that error appears in the above-identified patent and that said Letters Patent is hereby corrected as shown below:

Column 1, line 53, after "technician's" insert --tray for transport at the conclusion of the technician's--.

Column 2, line 32, delete "wieght" and insert therefor --weight--.

Column 5, line 60, change "crosssection" to --cross-section--.

Column 12, line 25, delete "rounding".

Signed and Sealed this

Twenty-sixth Day of March 1985

[SEAL]

Attest:

DONALD J. QUIGG

Attesting Officer

Acting Commissioner of Patents and Trademarks